United States Patent
Brunham (12)

(10) Patent No.: US 6,235,290 B1
(45) Date of Patent: *May 22, 2001

(54) DNA IMMUNIZATION AGAINST CHLAYMDIA INFECTION

(75) Inventor: Robert C. Brunham, Winnipeg (CA)

(73) Assignee: University of Manitoba, Winnipeg (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/893,381

(22) Filed: Jul. 11, 1997

(51) Int. Cl.[7] .................. A61K 39/118; A61K 39/00; C07K 1/00; C07K 16/00
(52) U.S. Cl. .................. 424/263.1; 424/185.1; 530/350; 530/389.5; 530/412
(58) Field of Search .................. 424/88, 92, 185.1, 424/263.1; 530/350, 389.5, 412

(56) References Cited

U.S. PATENT DOCUMENTS 5,589,466 * 12/1996 Felgner et al. .................. 514/44

FOREIGN PATENT DOCUMENTS 0 192 033A  8/1996  (EP) .

OTHER PUBLICATIONS

Fynan et al, "DNA vaccines: protective immunizations by parenteral, mucosal, and gene–gun inoculations" Proc. Natl. Acad. Sci., USA, 90:11478–11482. (No date), Dec. 1, 1993.*
Green et al, "Liposomal vaccines", Adv. Exp. Med. Biol., 383:83–92. (No date), Jun. 1, 1995.*
Baxby et al, "Potential use of nonreplicating vectors as recombinant vaccines", Vaccine, 10(1):8–9. (No date), Jan. 1, 1992.*
Anderson et al "Immune response in mice following immunization with DNA encoding fragment C of tetanus toxin", Inf. Immune., 64(8):3168–3173. (No date), Aug. 1, 1996.*
Kaul et al, "Expression of the Chlamydia trachomatis major outer membrane protein–encoding gene in Escherichia coli: role of the 3' end in mRNA stability", Gene, 87(1):97–104. (No date), Jan. 1, 1990.*
Douglas et al, "Mutagenesis of the P2 promoter of the major outer membrane protein gene of Chlamydia trachomatis", J. Bacteriol., 178(19):5573–5578. (No date), Oct. 1, 1996.*
Dascher et al, "Expression and translocation of the chlamydial major outer membrane protein in Escherichia coli", Microbiol Pathogenesis, 15:455–467. (No date), Dec. 1, 1993.*
Xu et al, Vaccine 12, 1534 (1994).

Moulder, Microbiol. Rev. 55, 143 (1991).
Schachter, Curr. Top. Microbiol. Immunol, 138, 109 (1988).
Hillis et al, N. Engl. J. Med. 334, 1399 (1996).
Brunham et al, Infectious Agents and Disease 3, 218 (1994).
Morrison et al, Advances in Host Defence Mechanisms, T.C. Quin, Ed. (Raven Press, New York, 1992), pp. 57–84.
Grayston et al, Sex Trans. Dis. 5, 73 (1978).
Grayston et al, J. I. Infect.Dis. 132, 87 (1975).
Taylor et al, Invest. Ophthalmol. Vis. Sci. 29, 1847 (1988).
Batteiger et al, J. Gen. Microbiol. 139, 2965 (1993).
Campos et al, Invest. Ophthalmol. Vis. Sci. 36, 1477 (1995).
Su, et al, Vaccine 13, 1023 (1995).
Tan, et al, Infect. Immun. 58, 3101 (1990).
Tuffrey, et al, J. Gen. Microbiol. 138, 1707 (1992).
Zhang, et al, Mol. Biol. Evol. 10, 1327 (1993).
Morrison, et al, Infect. Immun. 63, 4661 (1995).
Su, et al, Infect. Immun. 63, 3302 (1995).
Igietseme et al., Reg.Immunol. 5, 317 (1993).
Igietseme et al, Infect. Immun. 59, 1346 (1991).
Williams, et al, J. Infect. Dis. 149, 630(1984).
Tipples et al, J. Biol. Chem. 270, 7908 (1995).
Yang,et al, J. Immunol., 156, 4338 (1996).
Su, et al, Infect. Immun. 63, 946 (1995).
McWilliam, et al, J. Exp. Med. 179, 1331 (1994).
Neutra, et al, Annu. Rev. Immunol. 14, 275 (1996).
Austyn, J. Exp. Med. 183, 1287 (1996).
Brunham et al., J. Clin. Invest. 94, 458 (1994).
Brunham et al., J. Infect. Dis. 173 950 (1996).
Tang et al, Nature 1992, 356; 152–154.
Davis et al., Vaccine 1994, 12: 1503–1509.
Holland et al., Synthetic peptides based on Chlamydia trachomatis antigens identify systotoxic T lymphocyte responses in subjects from a trachoma–endemic population. Clin. Exp. Immunol Jan. 1997;107 (1): 44–49.
Donnelly et al., J. Infect. Dis. 713, 314 (1996).
Montgomery et al., DNA, Cell. Biol. 12, 777 (1993).
Donnelly et al., Nature Medicine 1, 583 (1995).
Rhodes et al., Dev. Biol. Stand. 82, 229 (1994).
Davis et al, Human Molecular Genetics 2, 1847 (1993).
Ulmer et al., Vaccine 12, 1541 (1994).
Xiang et al, Ertl. Immunity 2, 129 (1995).
Fynan et al, Proc. Natl. Acad. Sci. USA 90, 11478 (1993).
Manickan et al, J. Immunol. 155, 259 (1995).
Sedegah et al, Proc. Natl. Acad. Sci. USA 91, 9866 (1994).
Barry et al, Nature 377, 632 (1995).
Donnelly et al, Ann. N.Y. Acad. Sci. 772 (1995), pp. 40–46.

(List continued on next page.)

Primary Examiner—Rodney P. Swartz
(74) Attorney, Agent, or Firm—Sim & McBurney

(57) ABSTRACT

Nucleic acid, including DNA, immunization to generate a protective immune response in a host, including humans, to a major outer membrane protein of a strain of Chlamydia, preferably contains a nucleotide sequence encoding a MOMP or a MOMP fragment that generates antibodies that specifically react with MOMP and a promoter sequence operatively coupled to the first nucleotide sequence for expression of the MOMP in the host. The non-replicating vector may be formulated with a pharmaceutically-acceptable carrier for in vivo administration to the host.

9 Claims, 8 Drawing Sheets

OTHER PUBLICATIONS

[1] D. M. Pardoll and A. M. Beckerieg, Immunity 3, 165 (1995); [2] W.M. McDonnell and F. K. Askari, N. Engl. J. Med. 334, 42 (1996).
[1] J. B. Ulmer et al., Science 259, 1745 (1993); [2] B. Wang et al., Proc. Natl. Acad.. Sci. USA 90, 4156 (1993); [3] G. J. M. Cox, T.J. Zamb, L.A. Babiuk, J. Virol. 67, 5664 (1993); [4] E. Raz et al., Proc. Natl. Acad. Sci. USA, 91,9519 (1994);[5] Z.Q. Xiang et al., Virology 199, 132 (1994); [6] J.J. Donnelly et al., J. Infect. Dis. 713, 314 (1996);[7] D. L. Montgomery et al., DNA. Cell Biol. 12, 772 (1993); [8] J.J. Donnelly et al., Nature Medicine 1, 583 (1995); [13] E. F. Fynan et al, Proc. Natl. Acad. Sci. USA 90, 11478 (1993); [14] E. Manickan, R. J. D. Rouse, Z. Yu, J. Immunol. 155, 259 (1995).
[1] M. Sedegah, R. Hedstorm, P. Hobart, S. L. Hoffman, Proc. Natl. Acad. Sci. USA 91, 9866 (1994); [2] M. A. Barry, W.C. Lai, S.A. Johnston, Nature 377, 632 (1995); [4] D. B. Lowrie, R.E. Tascon, M. J. Colston, Vaccine 12, 1537 (1994).
J. W. Moulder, Microbiol. Rev. 55, 143 (1991).
[1] J. T. Grayston and S. –P. Wang, Sex Trans. Dis. 5, 73 (1978); [2]J.T. Grayston and S. –P Wang, J. I Infect.Dis. 132, 87 (1975).
[1] H. R. Taylor, J. Whittum–Hudson, J. Schachter, Invest. Ophthalmol. Vis. Sci. 29, 1847 (1988); [2] B.E. Batteiger, R. G. Rank, P.M. Bavoil, J. Gen. Microbiol. 139, 2965 (1993); [3] M. Campos et al., Invest. Ophthalmol. Vis. Sci. 36, 1477 (19950; [4] H. Su, M. Parne, H. D. Caldwell, Vaccine 13, 1023 (1995); [5] T.–W. Tan, A.J. Herring, I. E. Anderson, Infect. Immun. 58, 3101 91990).
Y.–X. Zhang, J. G. Fox, Y. Ho, Mol. Biol. Evol. 10, 1327 (1993).
[1] R. P. Morrison, K. Feilzer, D. B. Tumas, Infect. Immun. 63, 4661 (1995); [2] H. Su and H. D. Caldwell, Infect. Immun. 63, 3302 (1995); [3] J. U. Igietseme et al., Reg.Immunol. 5, 317 (1993); [4] J. U. Igietsemeand R. G. Rank, Infect. Immun. 59, 1346 91991);[5] D. M. Williams, J. Schachter, J. J. Coalson, J. Infect. Dis. 149, 630(1984).
G. Tipples and G. McClarty, J. Biol. Chem. 270, 7908 (1995).
X. Yang, K. T. HayGlass, R. C. Brunham, J. Immunol., 156, 4338 (1996).
H. Su and H. D. Caldwell, Infect. Immun. 63, 946 (1995).
[1] A. S. McWilliam, D. Nelson, J.A. Thomas, J. Exp. Med. 179, 1331 (1994); [3] J.M. Austyn, J. Exp. Med. 183, 1287 (1996).
R. C. Brunham et al., J. Infect. Dis. 173 950 (1996).
Tang et al., Nature 1992, 356: 152–154.
Furth et al., Vaccine 1994, 12: 1503–1509.
Morrison RP, Manning DS, Caldwell HD. Immunology of Chlamydia trachomatis infections: Immunoprotective and immunopathogenetic responses. In: Quin TC. Advances in host defence mechanisms. Sexually transmitted diseases. vol. 8, New York: Raven Press, 1992: 52–84.
Brunham R., Yang C., Maclean I., Kimani J., Maitha G., Plummer F., Chlamydia trachomatis from individuals in a sexually transmitted disease core group exhibit frequent sequence variation in the major outer membrane protein (ompl) gene. J. Clin. Invest. 1994; 94:458–63.
Xiang Z. Ertl HCJ. Manipulation of the immune response to a plasmid–encoded viral antigen by coinoculation with plasmids expressing cytokines. Immunity 1995: 2:129–35.

Holland M. J. et al. , Synthetic peptides based on Chlamydia trachomatis antigens identify sytotoxic T lymphocyte responses in subjects from a trachoma–endemic population. Clin. Exp. Immunol. Jan. 1997; 107 (1): 44–49.
Donnelly et al : "Protective efficacy of intramuscular immunization with naked DNA" Annals New York Academy of Sciences, vol. 772, 1995, pp. 40–46.
Lowrie, D.B. et al "Towards a DNA vaccine against tuberculosis", Vaccine, vol. 12, No. 16, 1994, pp. 1537–1540.
Lopez–Macia et al: "Induction of Antibodies against Salmonella typhi OmpC Porin by naked DNA immunization" Annalsof the New York Academy of Sciences, vol. 772, 1995, pp. 285–288.
Zhi Quan Xiang: "Vaccination with a plasmid vector carrying the Rabies virus glycoprotein gene induces protective immunity against rabies virus" Virology, vol. 199, 1994, pp. 132–140.
Xiang et al: "Manipulation of the Immune Response to a plasmid–encoded viral antigen by coinoculation with plasmids expressing cytokines" Immunity, vol. 2, Feb. 1995, pp. 129–135.
You–Xun Zhang et al: "Comparison of the major outer–membrane protein MOMP gene of mouse Pneumonitis (MOPN) and hamster SFPD strains of Chlamydia trachomatis with other Chlamydia strains" Molecular Biology and Evolution, vol. 10, No. 6, Nov. 1, 1993, pp. 1327–1342.
Pardoll, D.M. et al, Immunity 3, 165 (1995).
McDonnell et al, N. Engl. J. Med. 334, 42 (1996).
Ulmer et al., Science 259, 1745 (1993).
Wang et al., Proc. Natl. Acad. Sci. USA 90, 4156 (1993).
Cox et al, J. Virol. 67, 5664 (1993).
Raz, et al., Proc. Natl. Acad. Sci. USA, 91, 9519 (1994).
Donnelly et al, Ann. N.Y. Acad. Sci., 772, pp. 40–48, Jan. 1, 1995.*
Pardoll et al, Immunity, 3:165, Jan. 1, 1995.*
McDonnell et al, N. Engl. J. med. 334:42, Jan. 1, 1996.*
Ulmer et al, Science, 259:1745, Jan. 1, 1993.*
Wang et al, proc. Natl. Acad. Sci., USA 90:4156, Jan. 1, 1993.*
Cox et al, J. Virol. 67:5664, Jan. 1, 1993.*
Rax et al, proc. natl. cad. Sci. USA, 91:9519, Jan. 1, 1994.*
Xiang et al, Virol. 199:132, Jan. 1, 1994.*
Donnelly et al, J. Infect. Dis., 713:314, Jan. 1, 1994.*
Montgomery et al, DNA, Cell Biol. 12:772, Jan. 1, 1993.*
Donnelly et al, Nature, 1:583, Jan. 1, 1995.*
Fynan et al, Proc. natl. Acad. Sci. USA, 90:11478, Jan. 1, 1993.*
Manickan et al, J. Immunol. 155:259, Jan. 1, 1995.*
Sedegah et al, proc. Natl. Acad. Sci. USA, 91:9866, Jan. 1, 1994.*
Barry et al, nature 377:632, Jan. 1, 1995.*
Lowrie et al, Vaccine, 12:1537, Jan. 1, 1994.*
Moulder, Microbiol. Rev. 55:143, Jan. 1, 1991.*
Grayston et al, Sex Trans. Dis., 5:73, Jan. 1, 1978.*
Grayston et al, J. Infect. Dis., 132:87, Jan. 1, 1975.*
Taylor et al, Invest. ophthalmol. Vis. Sci. 29:1847, Jan. 1, 1988.*
Batteiger et al, j. Gen. Microbiol. 139:2965, Jan. 1, 1993.*
Campos et al, Invest. Ophthalmol. Vis. Sci. 36:1477, Jan. 1, 1995.*
Su et al, Vaccine, 13:1023, Jan. 1, 1995.*
Tan et al, Infect. Immun., 58:3101, Jan. 1, 1990.*
Zhang et al, Mol. Biol. Evol., 10:1327, Jan. 1, 1993.*
Morrison et al, Infect. Immun., 63:4661, Jan. 1, 1995.*

Su et al, Infect. Immun., 63:3302, Jan. 1, 1995.*
Igietseme et al, Reg. Immunol., 5:317, Jan. 1, 1993.*
Igietseme et al, Infect Immun., 59:1346, Jan. 1, 1991.*
Williams et al, J. Infect. Dis., 149:630, Jan. 1, 1984.*
Tipples et al, J. Biol. Chem., 270:7908, Jan. 1, 1995.*
Yang et al, J. Immunol., 156:4338, Jan. 1, 1996.*
Su et al, infect. Immun., 63:946, Jan. 1, 1995.*
McWilliam et al, J. Exp. Med, 179:1331, Jan. 1, 1994.*
Austyn, J. Exp. med., 183:1287, Jan. 1, 1996.*
Brunham et al, J. Infect. Dis., 173:950, Jan. 1, 1996.*
Tang et al, nature, 356:152–154, Jan. 1, 1992.*

Furth et al, Vaccine 12:1503–1509, Jan. 1, 1994.*
Morrison et al, in: Quin TC. Advances in host defence mechanisms. Sexually transmitted diseases. vol. * new York:Raven press, pp. 52–84, Jan. 1, 1992.*
Brunham et al, J. Clin. Invest., 94:458–463, Jan. 1, 1994.*
Xiang et al, Immunity, 2:129–135, Jan. 1, 1994.*
Holland et al, Clin. Exp. Immunol., 107(1):44–49, Jan. 1, 1997.*

* cited by examiner

A  B  C  D

86 KD —

51.6 KD —

MOMP —

34.1 KD —

DNA IMMUNIZATION AGAINST CHLAYMDIA INFECTION

FIELD OF INVENTION

The present invention relates to immunology and, in particular, to immunization of hosts using nucleic acid to provide protection against infection by Chlamydia.

BACKGROUND OF THE INVENTION

DNA immunization is an approach for generating protective immunity against infectious diseases (ref. 1—throughout this application, various references are cited in parentheses to describe more fully the state of the art to which this invention pertains. Full bibliographic information for each citation is found at the end of the specification, immediately preceding the claims. The disclosure of these references are hereby incorporated by reference into the present disclosure). Unlike protein or peptide based subunit vaccines, DNA immunization provides protective immunity through expression of foreign proteins by host cells, thus allowing the presentation of antigen to the immune system in a manner more analogous to that which occurs during infection with viruses or intracellular pathogens (ref. 2). Although considerable interest has been generated by this technique, successful immunity has been most consistently induced by DNA immunization for viral diseases (ref. 3). Results have been more variable with non-viral pathogens which may reflect differences in the nature of the pathogens, in the immunizing antigens chosen, and in the routes of immunization (ref. 4). Further development of DNA vaccination will depend on elucidating the underlying immunological mechanisms and broadening its application to other infectious diseases for which existing strategies of vaccine development have failed.

*Chlamydia trachomatis* is an obligate intracellular bacterial pathogen which usually remains localized to mucosal epithelial surfaces of the human host. Chlamydiae are dimorphic bacteria with an extracellular spore-like transmission cell termed the elementary body (EB) and an intracellular replicative cell termed the reticulate body (ref. 5). From a public health perspective, chlamydial infections are of great importance because they are significant causes of infertility, blindness and are a prevalent co-factor facilitating the transmission of human immunodeficiency virus type 1 (ref. 6). Protective immunity to *C. trachomatis* is effected through cytokines released by Th1-like CD 4 lymphocyte responses and by local antibody in mucosal secretions and is believed to be primarily directed to the major outer membrane protein (MOMP), which is quantitatively the dominant surface protein on the chlamydial bacterial cell and has a molecular mass of about 40 kDa (ref. 19).

Initial efforts in developing a chlamydial vaccine were based on parenteral immunization with the whole bacterial cell. Although this approach met with success in human trials, it was limited because protection was short-lived, partial and vaccination may exacerbate disease during subsequent infection episodes possibly due to pathological reactions to certain chlamydial antigens (ref. 8). More recent attempts at chlamydial vaccine design have been based on a subunit design using MOMP protein or peptides. These subunit vaccines have also generally failed, perhaps because the immunogens do not induce protective cellular and humoral immune responses recalled by native epitopes on the organism (ref. 9).

EP 192033 describes the provision of DNA construct for the expression, in vitro, of *Chlamydia trachomatis* MOMP polypeptides comprising the following operably linked elements:

a transcriptional promoter, a DNA molecule encoding a *C. trachomatis* MOMP polypeptide comprising a MOMP polynucleotide at least 27 base pairs in length from a sequence provided in Appendix A thereto, and a transcriptional terminator, wherein at least one of the transcriptional regulatory elements is not derived from *Chlamydia trachomatis*. There is no disclosure or suggestion in this prior art to effect DNA immunization with any such constructs.

WO 94/26900 describes the provision of hybrid picornaviruses which express chlamydial epitopes from MOMP of *Chlamydia trachomatis* and which is capable of inducing antibodies immuno-reactive with at least three different Chlamydia serovars. The hybrid picornavirus preferably is a hybrid polio virus which is attenuated for human administration.

SUMMARY OF THE INVENTION

The present invention is concerned with nucleic acid immunization, specifically DNA immunization, to generate in a host protective antibodies to a MOMP of a strain of Chlamydia. DNA immunization induces a broad spectrum of immune responses including TH1-like CD4 responses and mucosal immunity.

Accordingly, in one aspect, the present invention provides an immunogenic composition in vivo for in vivo administration to a host for the generation in the host of a protective immune response to a major outer membrane protein (MOMP) of a strain of Chlamydia, comprising a non-replicating vector comprising a nucleotide sequence encoding a MOMP or MOMP fragment that generates a MOMP-specific immune response, and a promoter sequence operatively coupled to said nucleotide sequence for expression of said MOMP in the host; and a pharmaceutically-acceptable carrier therefor.

The nucleotide sequence may encode a full-length MOMP protein or may encode a fragment, such as the N-terminal half of MOMP. The nucleotide sequence may encode a MOMP which stimulates a recall immune response following exposure to wild-type Chlamydia. The promoter may be the cytomegalovirus promoter.

The strain of Chlamydia may be a strain of Chlamydia inducing chlamydial infection of the lung, including *Chalamydia trachomatis* or *Chalamydia pneumoniae*. The non-replicating vector may be plasmid pcDNA3 into which the nucleotide sequence is inserted. The immune response which is stimulated may be predominantly a cellular immune response.

In a further aspect of the invention, there is provided as a method of immunizing a host against disease caused by infection with a strain of Chlamydia, which comprises administering to said host an effective amount of a non-replicating vector comprising a nucleotide sequence encoding a major outer membrane protein (MOMP) of a strain of Chlamydia or a MOMP fragment that generates a MOMP-specific immune response, and a promoter sequence operatively coupled to said nucleotide sequence for expression of said MOMP in the host.

In this aspect of the present invention, the various options and alternatives discussed above may be employed.

The non-replicating vector may be administrated to the host, including a human host, in any convenient manner, such as intramuscularly or intranasally. Intranasal administration stimulated the strongest immune response in experiments conducted herein.

The present invention also includes, in an additional aspect thereof, there is provided a method of using a gene encoding a major outer membrane protein (MOMP) of a strain of Chlamydia or MOMP fragment that generates a MOMP-specific immune response, to produce an immune response in a host, which comprises: isolating said gene, operatively linking said gene to at least one control sequence to produce a non-replicating vector, said control sequence directing expression of said MOMP when introduced into a host to produce an immune response to said MOMP, and introducing said vector into a host.

In a further aspect of the present invention provides a method of producing a vaccine for protection of a host against disease caused by infection with a strain of Chlamydia, which comprises isolating a nucleotide sequence encoding a major outer membrane protein (MOMP) of a strain of Chlamydia or a MOMP fragment that generates a MOMP-specific immune response, operatively linking said nucleotide sequence to at least one control sequence to produce a non-replicating vector, the control sequence directing expression of said MOMP when introduced to a host to produce an immune response to said MOMP, and formulating said vector as a vaccine for in vivo administration to a host.

Advantages of the present invention, therefore, include a method of obtaining a protective immune response to infection carried by a strain of Chlamydia by DNA immunization of DNA encoding the major outer membrane protein of a-strain of Chlamydia.

GENERAL DESCRIPTION OF THE INVENTION

Figure 1:
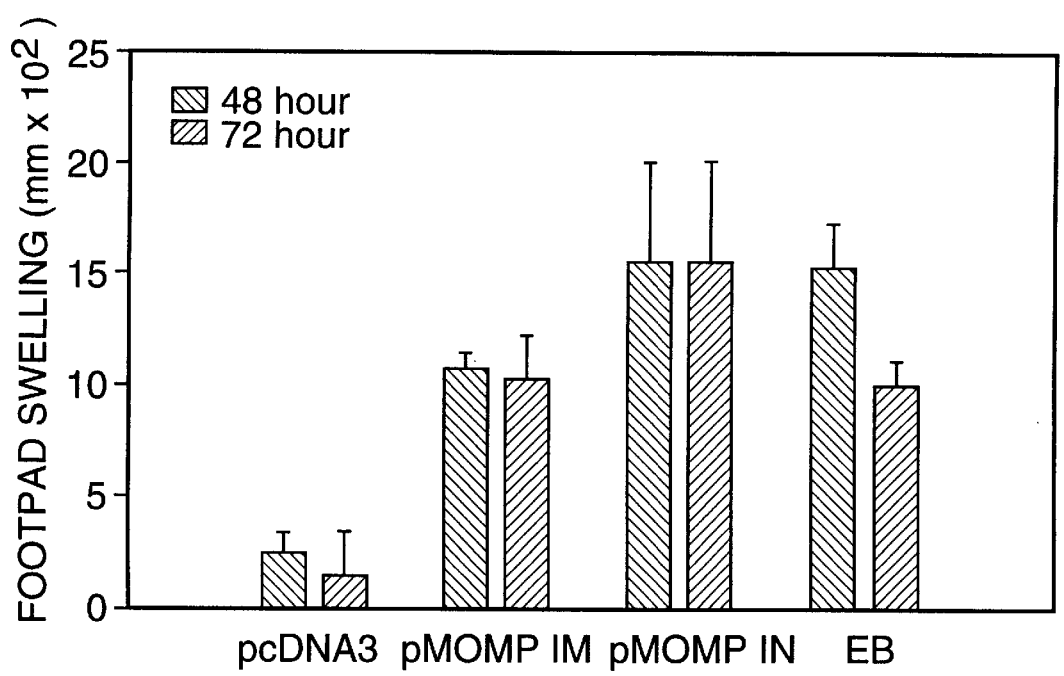
FIG. 1 illustrates delayed-type hypersensitively (DTH) responses following immunization. Balb/c mice (four per group) were immunized intramuscularly (pMOMP IM) or intranasally (pMOMP IN) with plasmid DNA containing the coding sequence of the MoPn MOMP gene or with MoPn elementary bodies (EB) at 0,3,6 weeks. The control group was treated with the blank plasmid vector (pcDNA3). Fifteen days after the last immunization, mice were tested for MoPn-specific DTH response as follows: 25 $\mu$l of heat-inactivated MoPn EB ($5 \times 10^4$ IFU) in SPG buffer was injected into the right hind footpad and the same volume of SPG buffer was injected into the left hind footpad. Footpad swelling was measured at 48H and 72H following the injection. The difference between the thickness of the two footpads was used as a measure of the DTH response. Data are shown as the mean±SEM.

To illustrate the present invention, plasmid DNA was constructed containing the MOMP gene from the *C. trachomatis* mouse pneumonitis strain (MoPn), which is a natural murine pathogen, permitting experimentation to be effected in mice. It is known that primary infection in the model induces strong protective immunity to reinfection. For human immunization, a human pathogen strain is used.

Any convenient plasmid vector may be used, such as pcDNA3, a eukaryotic II-selectable expression vector (Invitrogen, San Diego, Calif., USA), containing a cytomegalovirus promoter. The MOMP gene may be inserted in the vector in any convenient manner. The gene may be amplified from *Chlamydia trachomatic* genomic DNA by PCR using suitable primers and the PCR product cloned into the vector. The MOMP gene-carrying plasmid may be transferred, such as by electroporation, into *E. coli* for replication therein. Plasmids may be extracted from the *E. coli* in any convenient manner.

The plasmid containing the MOMP gene may be administered in any convenient manner to the host, such as intramuscularly or intranasally, in conjunction with a pharmaceutically-acceptable carrier. In the experimentation outlined below, it was found that intranasal administration of the plasmid DNA elicited the strongest immune response.

The data presented herein and described in detail below demonstrates that DNA immunization with the *C. trachoma-* tis MOMP gene elicits both cellular and humoral immune responses and produces significant protective immunity to lung challenge infection with *C. trachomatis* MoPn. The results are more encouraging than those obtained using recombinant MOMP protein or synthetic peptides and suggest that DNA immunization is an alternative method to deliver a chlamydial subunit immunogen in order to elicit the requisite protective cellular and humoral immune responses.

The data presented herein also demonstrate the importance in selection of an antigen gene for DNA immunization. The antigen gene elicits immune responses that are capable of stimulating recall immunity following exposure to the natural pathogen. In particular, injection of a DNA expression vector encoding the major outer surface protein (the pMOMP) but not one encoding a cytoplasmic enzyme (CTP synthetase) of *C. trachomatis* generated significant protective immunity to subsequent chlamydial challenge. The protective immune response appeared to be predominantly mediated by cellular immunity and not by humoral immunity since antibodies elicited by DNA vaccination did not bind to native EBs. In addition, MOMP DNA but not CTP synthetase DNA immunization elicited cellular immunity readily recalled by native EBs as shown by positive DTH reactions.

In addition, mucosal delivery of MOMP DNA is demonstrated herein to be significantly more efficient in inducing protective immunity to *C. trachomatis* infection than intramuscular injection. This may be relevant to the nature of *C. trachomatis* infection which is essentially restricted to mucosal surfaces and the efficiency of antigen presentation (ref. 14). The rich population and rapid recruitment of dendritic cells into the respiratory epithelium of the lung may be relevant to the enhanced efficacy of intranasal DNA immunization experiments (ref. 15). The data presented herein represents the demonstration of a first subunit chlamydial vaccine which engenders substantial protective immunity.

Additionally, it may be possible to amplify (and/or canalize) the protective immune response by co-administration of DNAs that express immunoregulatory cytokines in addition to the antigen gene in order to achieve complete immunity (ref. 21) The use of multiple antigen genes from chlamydiae may augment the level of protective immunity achieved by DNA vaccination.

A possible concern regarding MOMP DNA immunization stems from the observation that the MOMP among human *C. trachomatis* strains is highly polymorphic (ref. 16) and hence it may be difficult to generate a universal chlamydial vaccine based on this antigen gene. One way to solve this problem may be to search for conserved protective epitope (s) within the MOMP molecule. Another, possibly more feasible way, is to design a multivalent vaccine based on multiple MOMP genes. The latter approach is justified by the fact that the inferred amino acid sequences of MOMP among related serovars is relatively conserved and the repertoire of *C. trachomatis* genevariants appears to be finite (ref. 16).

It is clearly apparent to one skilled in the art, that the various embodiments of the present invention have many applications in the fields of vaccination, diagnosis and treatment of chlamydial infections. A further non-limiting discussion of such uses is further presented below.

1. Vaccine Preparation and Use

Immunogenic compositions, suitable to be used as vaccines, may be prepared from the MOMP genes and vectors as disclosed herein. The vaccine elicits an immune response in a subject which includes the production of anti-MOMP antibodies. Immunogenic compositions, including vaccines, containing the nucleic acid may be prepared as injectables, in physiologically-acceptable liquid solutions or emulsions for polynucleotide administration. The nucleic acid may be associated with liposomes, such as lecithin liposomes or other liposomes known in the art, as a nucleic acid liposome (for example, as described in WO 9324640, ref. 12) or the nucleic acid may be associated with an adjuvant, as described in more detail below. Liposomes comprising cationic lipids interact spontaneously and rapidly with polyanions, such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. Published PCT application WO 94/27435 describes compositions for genetic immunization comprising cationic lipids and polynucleotides. Agents which assist in the cellular uptake of nucleic acid, such as calcium ions, viral proteins and other transfection facilitating agents, may advantageously be used.

Polynucleotide immunogenic preparations may also be formulated as microcapsules, including biodegradable time-release particles. Thus, U.S. Pat. No. 5,151,264 describes a particulate carrier of a phospholipid/glycolipid/polysaccharide nature that has been termed Bio Vecteurs Supra Moléculaires (BVSM). The particulate carriers are intended to transport a variety of molecules having biological activity in one of the layers thereof.

U.S. Pat. No. 5,075,109 describes encapsulation of the antigens trinitrophenylated keyhole limpet hemocyanin and staphylococcal enterotoxin B in 50:50 poly (DL-lactideco-glycolide). Other polymers for encapsulation are suggested, such as poly(glycolide), poly(DL-lactide-co-glycolide), copolyoxalates, polycaprolactone, poly(lactide-co-caprolactone), poly(esteramides), polyorthoesters and poly (8-hydroxybutyric acid), and polyanhydrides.

Published PCT application WO 91/06282 describes a delivery vehicle comprising a plurality of bioadhesive microspheres and antigens. The microspheres being of starch, gelatin, dextran, collagen or albumin. This delivery vehicle is particularly intended for the uptake of vaccine across the nasal mucosa. The delivery vehicle may additionally contain an absorption enhancer.

The MOMP gene containing non-replicating vectors may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously, intravenously, intradermally or intramuscularly, possibly following pretreatment of the injection site with a local anesthetic. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkylene glycols or triglycerides. Oral formulations may include normally employed incipients, such as, for example, pharmaceutical grades of saccharine, cellulose and magnesium carbonate.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize the MOMP and antibodies thereto, and if needed, to produce a cell-mediated immune response. Precise amounts of active ingredient required to be administered depend on the judgment of the practitioner. However, suitable dosage ranges are readily determinable by one skilled in the art and may be of the order of about 1 µg to about 1 mg of the MOMP gene-containing vectors. Suitable regimes for initial administration and booster doses are also variable, but may include an initial administration followed by subsequent administrations. The dosage may also depend on the route of administration and will vary according to the size of the host. A vaccine which protects against only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the vectors are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Thus, adjuvants have been identified that enhance the immune response to antigens. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines.

A wide range of extrinsic adjuvants and other immunomodulating material can provoke potent immune responses to antigens. These include saponins complexed to membrane protein antigens to produce immune stimulating complexes (ISCOMS), pluronic polymers with mineral oil, killed mycobacteria in mineral oil, Freund's complete adjuvant, bacterial products, such as muramyl dipeptide (MDP) and lipopolysaccharide (LPS), as well as monophoryl lipid A, QS 21 and polyphosphazene.

In particular embodiments of the present invention, the non-replicating vector comprising a first nucleotide sequence encoding a MOMP gene of Chlamydia may be delivered in conjunction with a targeting molecule to target the vector to selected cells including cells of the immune system.

The non-replicating vector may be delivered to the host by a variety of procedures, for example, Tang et al. (ref. 17) disclosed that introduction of gold microprojectiles coated with DNA encoding bovine growth hormone (BGH) into the skin of mice resulted in production of anti-BGH antibodies in the mice, while Furth et al. (ref. 18) showed that a jet injector could be used to transfect skin, muscle, fat and mammary tissues of living animals.

2. Immunoassays

The MOMP genes and vectors of the present invention are useful as immunogens for the generation of anti-MOMP antibodies for use in immunoassays, including enzyme-linked immunosorbent assays (ELISA), RIAs and other non-enzyme linked antibody binding assays or procedures known in the art. In ELISA assays, the non-replicating vector first is administered to a host to generate antibodies specific to the MOMP. These MOMP specific antibodies are immobilized onto a selected surface, for example, a surface capable of binding the antibodies, such as the wells of a polystyrene microtiter plate. After washing to. remove incompletely adsorbed antibodies, a nonspecific protein, such as a solution of bovine serum albumin (BSA) that is known to be antigenically neutral with regard to the test sample, may be bound to the selected surface. This allows for blocking of nonspecific adsorption sites on the immobilizing surface. and thus reduces the background caused by nonspecific bindings of antisera onto the surface.

The immobilizing surface is then contacted with a sample, such as clinical or biological materials, to be tested in a manner conducive to immune complex (antigen/antibody) formation. This procedure may include diluting the sample with diluents, such as solutions of BSA, bovine gamma globulin (BGG) and/or phosphate buffered saline (PBS)/Tween. The sample is then allowed to incubate for from about 2 to 4 hours, at temperatures such as of the order of about 20° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound MOMP specific antibodies, and subsequent washing, the occurrence, and even amount, of immunocomplex formation may be determined.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

This Example illustrates the preparation of a plasmid vector containing the MOMP gene.

pMOMP expression vector was made as follows. The MOMP gene was amplified from *Chlamydia trachomatis* mouse pneumonitis (MoPn) strain genomic DNA by polymerase chain reaction (PCR) with a 5' primer (GGGGATCCGCCACCATGCTGCCTGTGGGGAATCCT) (SEQ ID NO: 1) which includes a BamH1 site, a ribosomal binding site, an initiation codon and the N-terminal sequence of the mature MOMP of MoPn and a 3' primer (GGGGCTCGAGCTATTAACGGAACTGAGC) (SEQ ID NO: 2) which includes the C-terminal sequence of the MoPn MOMP, a XhoI site and a stop codon. The DNA sequence of the MOMP leader peptide gene sequence was excluded. After digestion with BamHl and XhoI, the PCR product was cloned into the pcDNA3 eukaryotic II-selectable expression vector (Invitrogen, San Diego) with transcription under control of the human cytomegatovirus major intermediate early enhancer region (CMV promoter). The MOMP gene-encoding plasmid was transferred by electroporation into *E. coli* DH5αF which was grown in LB broth containing 100 µg/ml of ampicillin. The plasmids was extracted by Wizard™ Plus Maxiprep DNA purification system (Promega, Madison). The sequence of the recombinant MOMP gene was verified by PCR direct sequence analysis, as described (ref. 20). Purified plasmid DNA was dissolved in saline at a concentration of 1 mg/ml. The DNA concentration was determined by a DU-62 spectrophotometer (Beckman, Fullerton, Calif.) at 260 nm and the size of the plasmid was compared with DNA standards in ethidium bromide-stained agarose gel.

Figure 7:
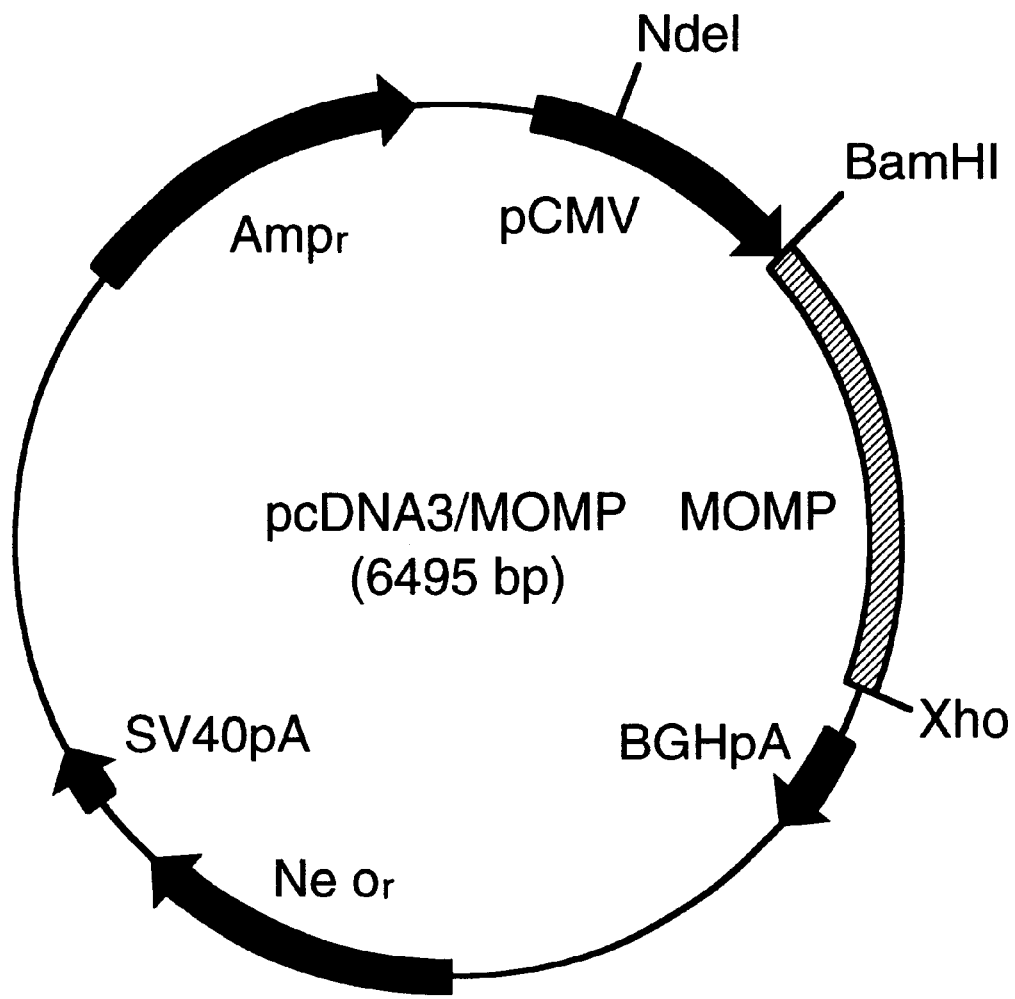
FIG. 7 shows the elements and construction of plasmid pcDNA3/MOMP.

The MOMP gene containing plasmid, pcDNA3/MOMP is illustrated in FIG. 7.

Example 2

This Example illustrates DNA immunization of mice and the results of DTH testing.

A model of murine pneumonia induced by the *C. trachomatis* mouse pneumonitis strain [MoPn] was used (ref. 11). Unlike most strains of *C. trachomatis* which are restricted to producing infection and disease in humans, MoPn is a natural murine pathogen. It has previously been demonstrated that primary infection in this model induces strong protective immunity to reinfection. In addition, clearance of infection is related to CD4 Th1 lymphocyte responses and is dependent on MHC class II antigen presentation (ref. 11).

For experimental design, groups of 4 to 5 week old female Balb/c mice (5 to 13 per group) were immunized intramuscularly (IM) or intranasally (IN) with plasmid DNA containing the coding sequence of the MoPn MOMP gene (1095 bp), prepared as described in Example 1, or with the coding sequence of the *C. trachomatis* serovar $L_2$ CTP synthetase gene (1619 bp (refs. 10, 12), prepared by a procedure analogous described in Example 1. CTP synthetase is a conserved chlamydial cytoplasmic enzyme catalizing the final step in pyrimidine biosynthesis and is not known to induce protective immunity. Negative control animals were injected with saline or with the plasmid vector lacking an inserted chlamydial gene.

For IM immunization, both quardiceps were injected with 100 μg DNA in 100 μl of saline per injection site on three occasions at 0, 3 and 6 weeks. For IN immunization, anaesthetized mice aspirated 25 μl of saline containing 50 μg DNA on three occasions at 0, 3 and 6 weeks. As a positive control, a separate group of mice received $5 \times 10^6$ inclusion forming units (IFUs) of MoPn EBs administered intraperitoneally in incomplete Freund's adjuvant according to the above schedule. At week 8, all groups of mice had sera collected for measuring antibodies and were tested for delayed-type hypersensitivity (DTH) to MoPn Ebs by footpad injection (ref. 13).

A positive 48 and 72 hour DTH reaction was detected among mice immunized with MOMP DNA or with MoPn Ebs but not among mice immunized with the blank vector (see FIG. 1). The DTH reaction elicited with MOMP DNA delivered intranasally was comparable to that observed among mice immunized with EBs. No DTH reaction was detected among the groups of mice vaccinated with CTP synthetase DNA (see Table 1 below). Thus, injection of MOMP DNA generated a DTH reaction that was capable of recall by naturally processed peptides from *C. trachomatis* EBs while injection of CTP synthetase DNA failed to do so.

Example 3

This Example illustrates DNA immunization of mice and the generation of antibodies.

Figure 2A:
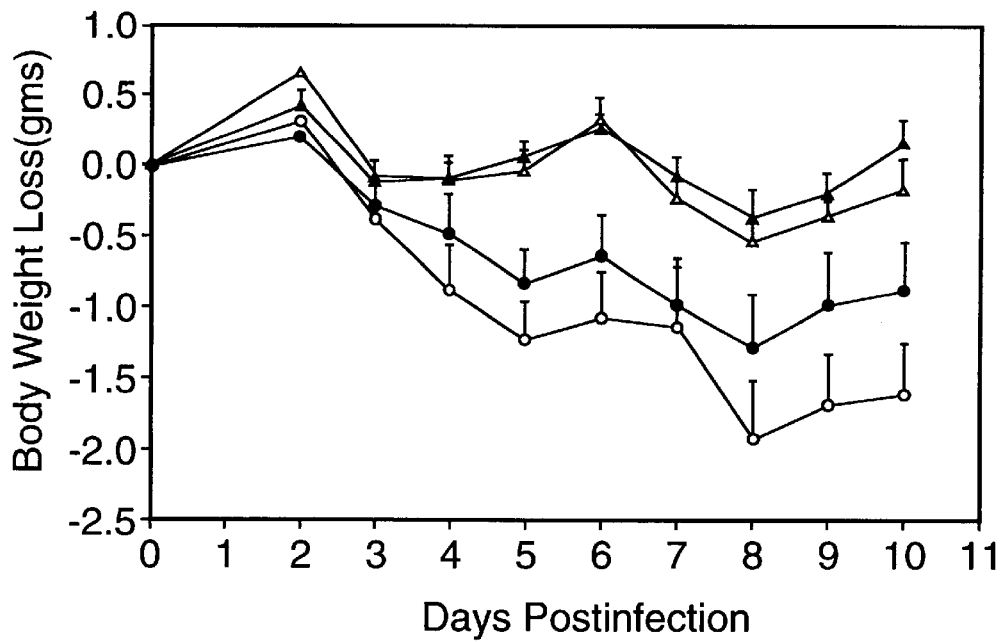
FIG. 2, having panels A and B, illustrate protection against MoPn infection with momp gene products following DNA immunization. The Balb/c mice were immunized with (○) pcDNA3 (n=11), (•) pMOMP intramuscularlly (n=12), (Δ) pMOMP intranasally (n=5) or (▲) MoPn EBs (n=12). Eighteen days after the last immunization, mice were challenged intranasally with infectious MoPn (1000 IFU). Panel A shows body weight loss. Body weight was measured daily following infection challenge and each point represents the mean±SEM of the body weight loss. Panel B shows in vivo chlamydia clearance. Mice were sacrifced day 10 postinfection and recovery of infectious MoPn from lung tissue was analyzed by quantitative tissue culture in order to determine the in vivo chlamydial clearance. The data represent mean±SEM of the $\log_{10}$ IFU per lung.
Figure 2B:
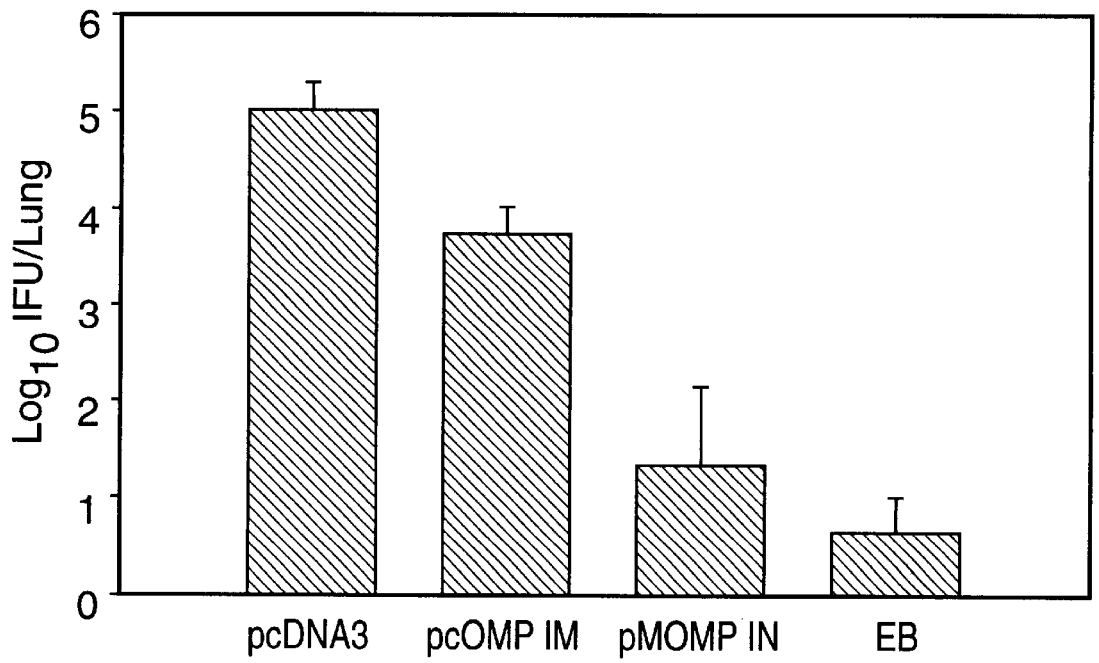
Figure 3:
FIG. 3 illustrates detection of serum antibody to MoPn MOMP in DNA immunized mice by immunoblot analysis. Day 60 pooled sera from mice immunized with MoPn EBs (Lane A), pMOMP (Lane B), blank pcDNA3 vector (Lane C) or saline (Lane D), were diluted at 1:100 and reacted with purified MoPn EBs that had been separated in a 10% SDS-polyacrylamide gel and transferred to a nitrocellulose membrane.
Figure 4A:
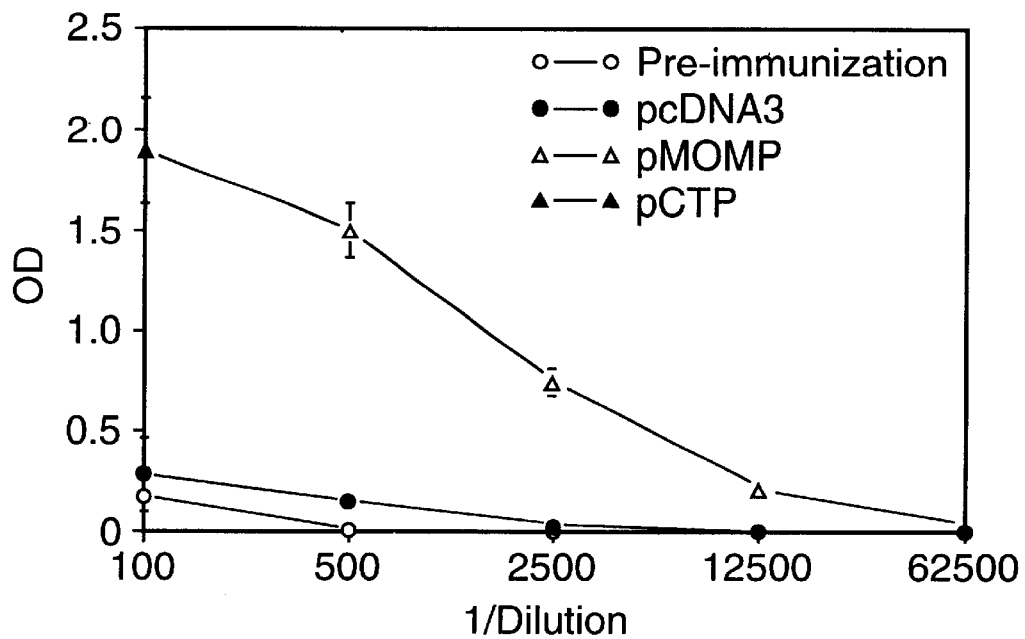
FIG. 4, having panels A, B, C and D, compares serum 1gG subclasses $1gG_{2a}$ (Panels A and C) with lgG, Panels B and D) against recombinant MOMP protein (Panels A and B) or MoPn EBs (Panels C and D) induced by DNA immunization. Mice were non-immunized or immunized intramuscularly with pMOMP, CTP synthetase DNA (pCTP) or the blank plasmid vector (pcDNA3) at 0,3,6 weeks and pooled sera from each group were collected two weeks following the last immunization (day 10). The data represent mean±SEM of the OD value of four duplicates.
Figure 4B:
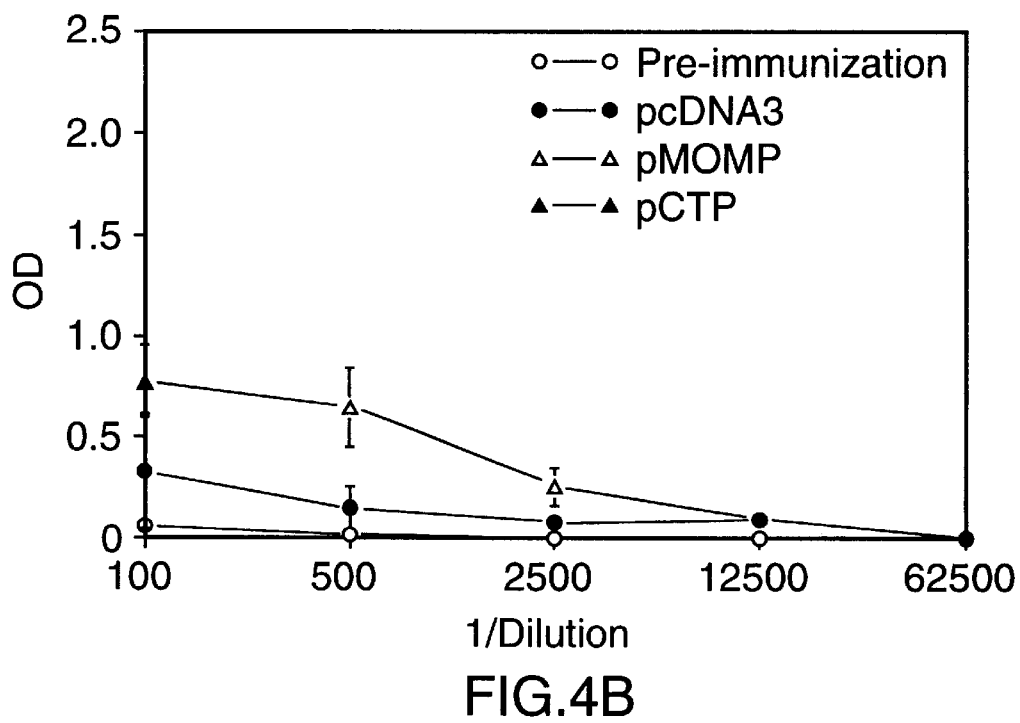
Figure 4C:
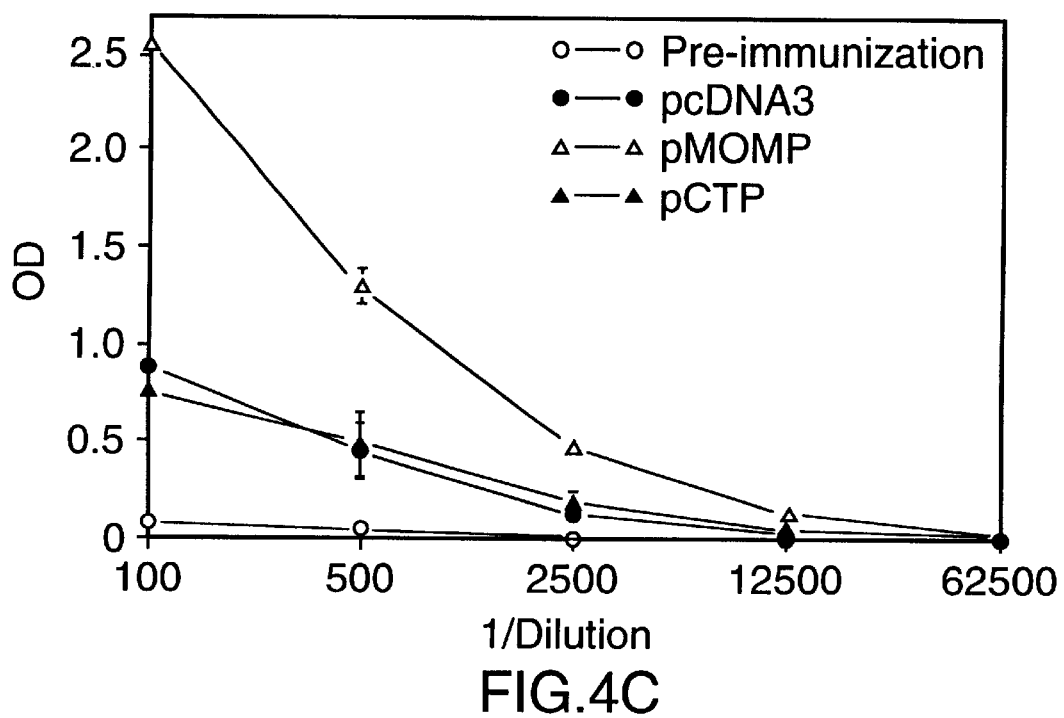
Figure 4D:
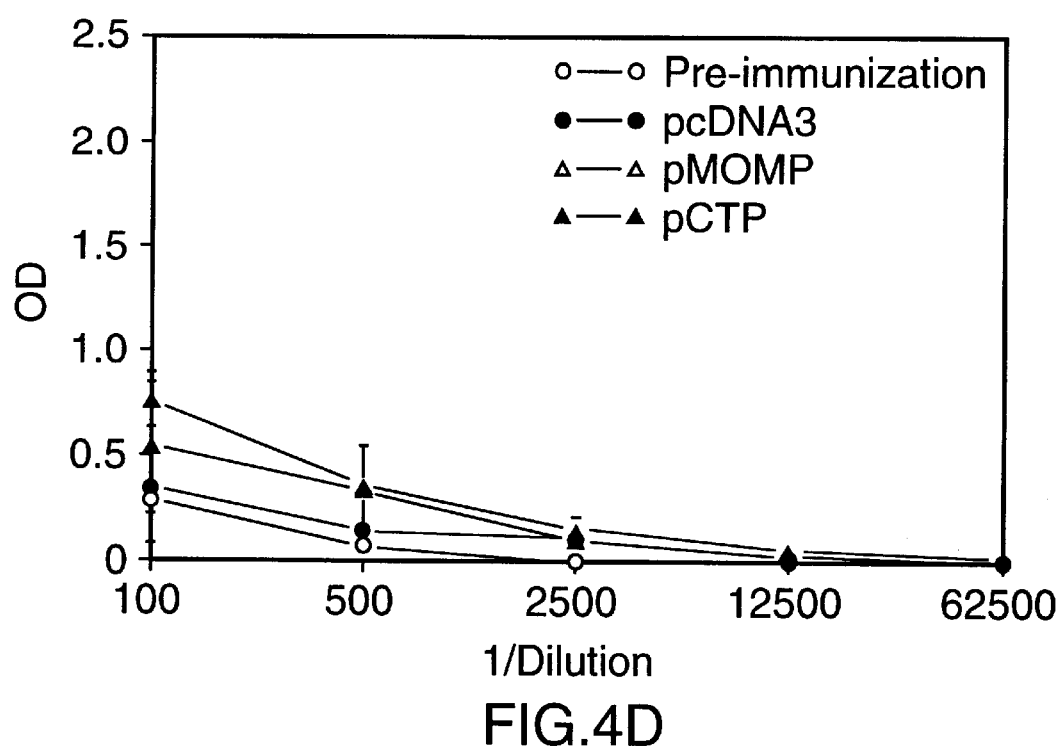

Injection of CTP synthetase DNA as described in Example 2 resulted in the production of serum antibodies to recombinant CTP synthetase (Table 1) (ref. 14). Antigen-specific serum Abs were measured by ELISA. Flat-bottom 96-well plates (Corning 25805, Corning Science Products, Corning, N.Y.) were coated with either recombinant chlamydial CTP-synthetase (1 μg/ml) or purified MoPn EBs ($6 \times 10^4$ IFU/well) overnight at 4° C. The Plates were rinsed with distilled water and blocked with 4% BSA PBS-Tween and 1% low fat skim milk for 2 hours at room temperature. Dilutions of sera samples were performed in 96-well round bottom plates immediately prior to application on the antigen coated plates. The plates were incubated overnight at 4° C. and washed ten times. Biotinylated goat anti-mouse IgG1 or goat anti-mouse IgG2a (Southern Biotechnology Associates, Inc. Birmingham, Ala.) were next applied for 1 hour at 37° C. After washing, streptoavidin-alkaline phosphatase conjugate (Jackson ImmunoResearch Laboratories, Inc. Mississagua, Ontario, Canada) were added and incubated at 37° C. for 30 min. Following another wash step, phosphatase substrate in phosphatase buffer (pH 9.8) was added and allowed to develop for 1 hour. Th plates were read at 405 nm on a BIORAD 3550 microplate reader.

lgG2a antibody titers were approximately 10-fold higher than lgG1 antibody titers suggesting that DNA immunization elicited a more dominant $T_{H1}$-like response. Injection of MOMP DNA as described in Example 2 resulted in the production of serum antibodies to MOMP (Table 2) as detected in an immunoblot assay (FIG. 2). However, neither CTP synthetase DNA nor MOMP DNA immunized mice produced antibodies that bound to native *C. trachomatis* EBs (Table 1), suggesting that the antibody responses may not to be the dominantly protective mechanism. A comparison of serum lgG subclasses, lgG2a (Panels A and C and lgG$_1$ (Panels B and D) against MOMP protein (Panels A and B) or MoPn (Panels C and D) induced by DNA immunization as described above, is contained in FIG. 4.

Example 4

This Example illustrates DNA immunization of mice to achieve protection.

To investigate whether a cell-mediated immune response elicited by MOMP DNA was functionally significant, in vivo protective efficacy was evaluated in mice challenged intranasally with $1 \times 10^3$ IFU of *C. trachomatis* MoPn. To provide a measure of Chlamydia-induced morbidity, the loss in body weight was measured over 10 days following challenge with *C. trachomatis* (see FIG. 2, Panel A). Mice injected with the unmodified vector were used as negative controls and mice immunized with EBs were used as positive controls. Mice immunized with MOMP DNA intranasally maintained a body weight comparable to that observed among EB immunized mice. Mice intramuscularly immunized with MOMP DNA lost body mass but did so at a rate less than the negative control group.

Figure 5A:
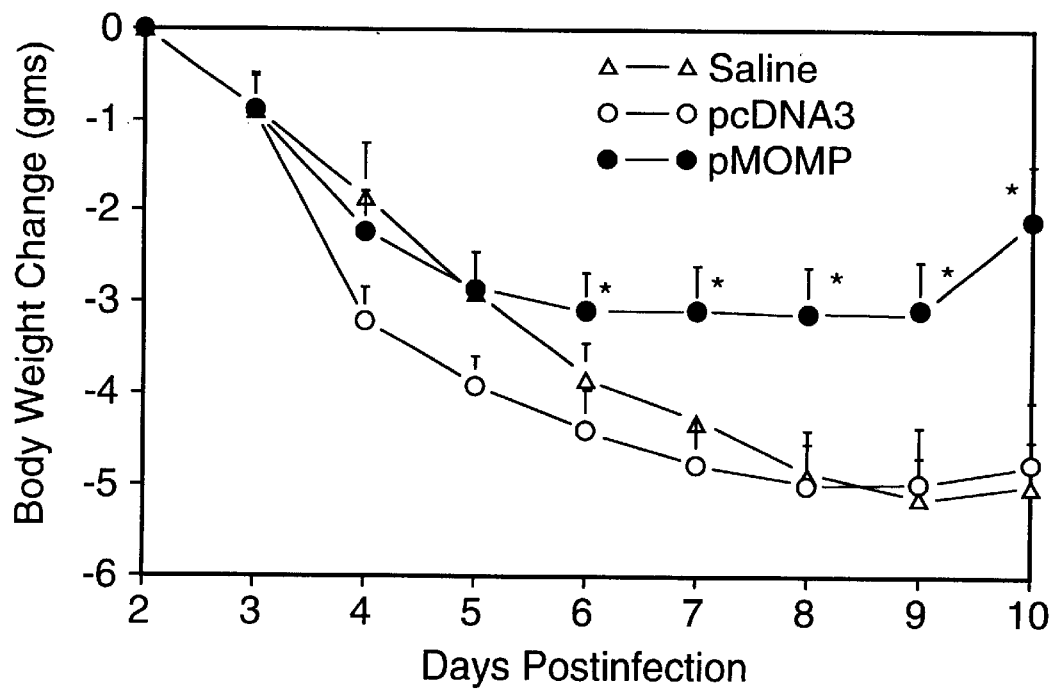
FIG. 5, having panels A and B, demonstrates that DNA vaccination with the MOMP gene enhanced clearance of MoPn infection in the lung. Groups of Balb/c mice were immunized with pMOMP (N=10), pcDNA3 (N=10) or saline (N=5). Eighteen days after the last immunization, the mice were challenged intranasally with infectious MoPn ($10^4$ IFU). Panel A shows the body weight of the mice measured daily following challenge infection until the mice were sacrificed at day 10. Each point represents the mean±SEM of the body weight change. * represents P<0.05 compared with pcDNA3 treated group. Panel B: the mice were sacrificed at day 10 postinfection and the MoPn growth in the lung was analyzed by quantitative tissue culture. The data represent mean±SEM of the $\text{Log}_{10}$IFU per lung. * represents P<0.01 compared with pcDNA3 treated group.
Figure 5B:
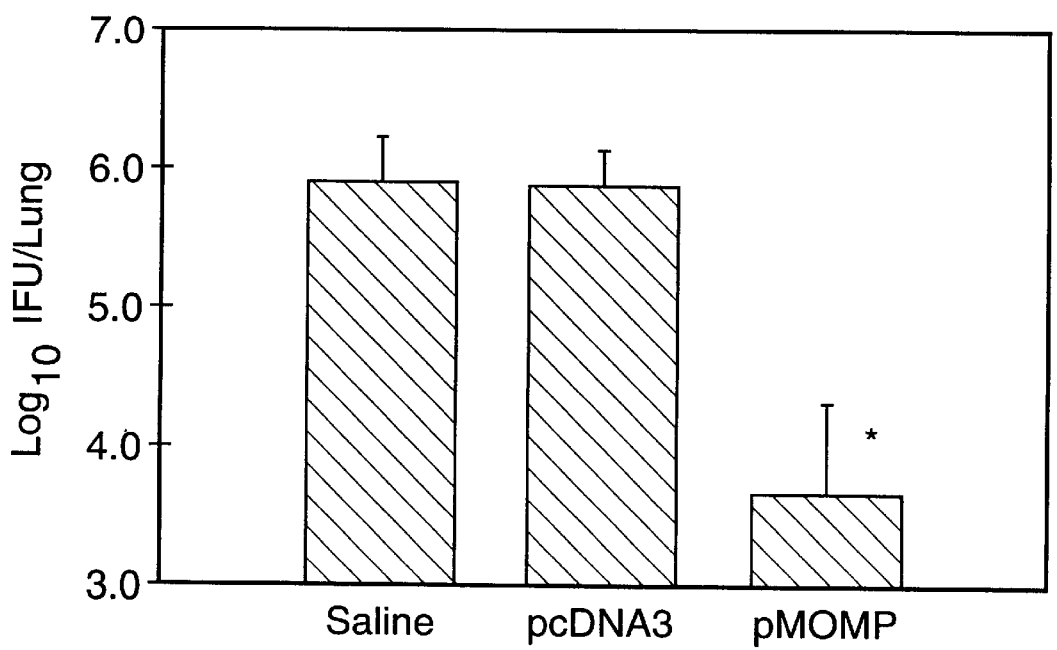
Figure 6A:
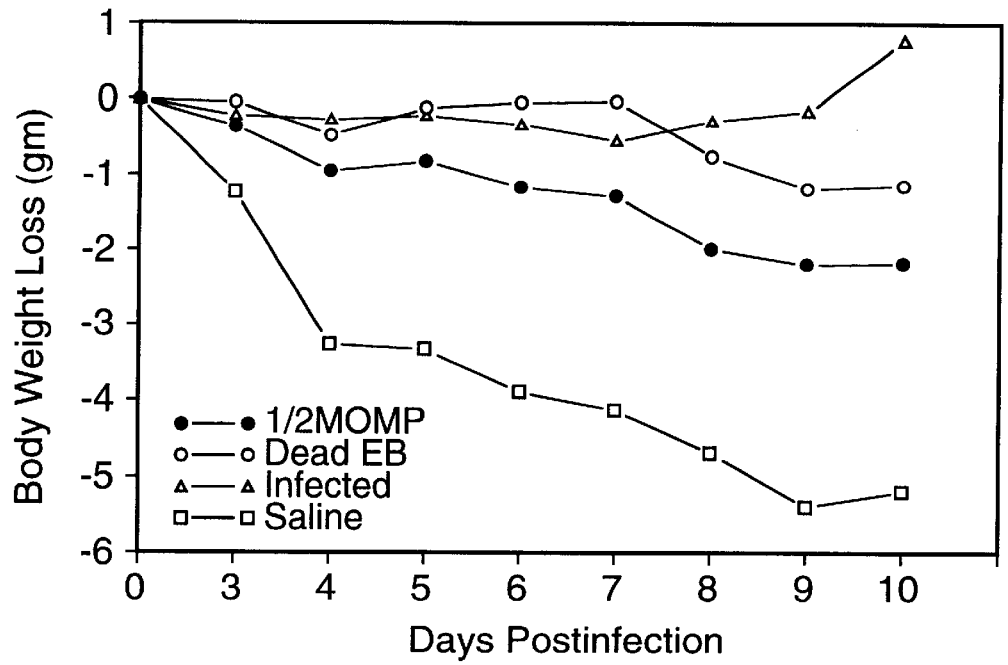
FIG. 6, having panels A and B, shows evaluation of the responses of mice to MoPn intranasal challenge infection. In Panel A, is shown change in body weight post challenge and in Panel B, is shown the growth of MoPn in lung tissue collected 10 days after challenge. Mice were sham immunized (✕), immunized intraperitoneally with MoPn EBs (when called ○), recovered from prior MoPn lung infection (▲) or immunized intramuscularly with p½ MOMP (•).
Figure 6B:
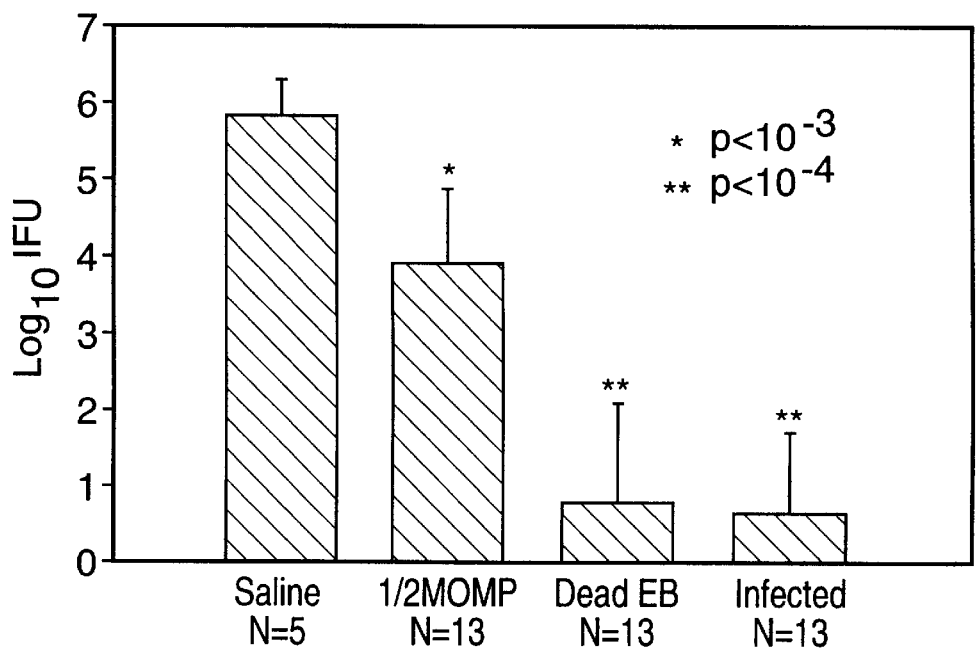

A more direct measure of the effectiveness of DNA vaccination is the ability of mice immunized with MOMP DNA to limit the in vivo growth of Chlamydia following a sublethal lung infection. Day 10 post-challenge is the time of peak growth (ref. 13) and was chosen for comparison of lung titers among the various groups of mice. Mice intranasally immunized with MOMP DNA had chlamydial lung titers that were over 1000-fold lower ($\log_{10}$ IFU 1.3±0.3; mean±SEM ) than those of control mice immunized with the blank vector ($\log_{10}$ IFU 5.0±0.3; p<0.01) (see FIG. 2, Panel B). Mice intramuscularly immunized with MOMP DNA had chlamydial lung titers that were more than 10-fold lower than the unmodified vector group (p=0.01). Mice intranasally immunized with MOMP DNA had significantly lower chlamydial lung titers than mice immunized with MOMP DNA intramuscularly ($\log_{10}$ IFU 1.3±0.8 versus $\log_{10}$ IFU 0.66±0.3 respectively; p=0.38). The substantial difference (2.4 logs) in chlamydial lung titers observed between the intranasally and intramuscularly MOMP DNA immunized mice suggests that mucosal immunization is more efficient at inducing immune responses to accelerate chlamydial clearance in the lung. The lack of protective effect with the unmodified vector control confirms that DNA per se was not responsible for the immune response. Moreover, the absence of protective immunity following immunization with CTP synthetase DNA confirms that the immunity was specific to the MOMP DNA (see Table 1). FIG. 5 shows similar challenge data at a higher challenge dose.

Example 5

This Example describes the construction of p½MOMP.

A PCR cloned MoPn gene was constructed containing a deletion mutation in codon 177. This recitation yields a truncated MOMP protein containing approximately 183 amino-terminal amino acids (ref. 10). This construct, termed p½MOMP, was cloned into the vector pcDNA3 (Invitrogen), in the manner described in Example 1.

Example 6

This Example illustrates immunization of mice with p½MOMP.

Balb/c mice were immunized in the quadriceps three times at a three week intervals with 100 $\mu$g of p½MOMP DNA.

Fifteen days after the last immunization and 60 days after the first injection, mice were bled for measurement of serum antibodies of MoPn EBs in an EIA assay and were injected in the footpad with 25 $\mu$l ($5\times10^4$ inclusion forming units) of heat killed EBs for measurement of DTH which was measured at 72 hours (ref. 13). Mice were intranasally challenged with 1000 infectious units of MoPn and their body weight measured daily for the subsequent 10 days. At that time, mice were sacrificed and quantitative cultures of MoPn in the lung determined (ref. 13).

Table 3 shows that p½MOMP immunization elicited a positive DTH response to footpad injection of MoPn EBs. Low titers (approximate titer 1/100) serum antibodies to surface determinants on EBs were also detected at day 60 post vaccination. Immunization with the unmodified vector elicited neither serum antibodies nor a DTH response. FIG. 6, Panel A shows that p½MOMP immunization evoked a protective immune response to MoPn challenge as measured by change in body weight post infection and by the in vivo growth of MoPn in lung tissue day 10 post challenge. The in vivo growth among saline treated mice was $\log_{10}$ 5.8±0.21 and among p½MOMP immunized mice was $\log_{10}$ 3.9±0.25, p<.001, FIG. 2, Panel B. As a positive control, mice immunized with heat killed MoPn EBs or recovered from prior lung infection with MoPn were markedly and equivalently protected against challenged infection (p<.0001).

As may be seen in this Example, using a frame-shift deletion mutant at codon 177 of the MOMP gene, significant protective immunity to challenge infection was elicited suggesting that protective sites can be found in the amino terminal half of the protein.

SUMMARY OF DISCLOSURE

In summary of this disclosure, the present invention provides a method of nucleic acid, including DNA, immunization of a host, including humans, against disease caused by infection by strain of Chlamydia, specifically *C. trachomatis*, employing a non-replicating vector, specifically a plasmid vector, containing a nucleotide sequence encoding a major outer membrane protein (MOMP) of a strain of Chlamydia and a promoter to effect expression of MOMP in the host. Modifications are possible within the scope of this invention.

TABLE 1

Serum antibody titers and delayed-type hypersensitivity (DTH) responses and in vivo growth of *Chlamydia trachomatis* following pCTP synthetase or MoPn EB immunization. Results are presented as means ± SEM

| | anti-MoPn EB antibodies ($\log_{10}$) | | anti-rCTP synthetase antibodies ($\log_{10}$) | | anti-EB DTH | $\log_{10}$ IFU/lung d10 post |
|---|---|---|---|---|---|---|
| | IgG1 | IgG2a | IgG1 | IgG2a | (mm × $10^2$) | challenge |
| Saline (n = 9) | <2 | <2 | <2 | <2 | 4.5 ± 1.5 | 4.9 ± .24 |
| pCTP synthetase (n = 11) | <2 | <2 | 3.8 ± .3 | 4.7 ± .1 | 1.4 ± 1.5 | 4.7 ± .13 |
| EB (n = 4) | 5.0 ± .2 | 4.8 ± .3 | 3.6 ± .8 | 2.9 ± 0 | 15.2 ± 2.0 | 0 |

TABLE 2

Serum antibody Elisa titers to *Chlamydia trachomatis* mouse pneumonitis recombinant MOMP and EBs were measured 60 days after the initial immunization among mice immunized with blank vector alone (pcDNA3), vector containing the MOMP gene (pMOMP) and vector containing the CTP synthetase gene (pCTP). Non-immunized mice were also tested.

| | rMOMP | | EB | |
|---|---|---|---|---|
| Immunogen | IgG2a | IgG1 | IgG2a | IgG1 |
| pcDNA3 | <2.6* | <2.6 | <2.6 | <2.6 |
| pMOMP | 3.77 ± 0.1 | 2.90 ± 0.14 | 3.35 ± 0.11 | <2.6 |
| pCTP | ND | ND | <2.6 | <2.6 |
| Preimmunization | <2.6 | <2.6 | <2.6 | <2.6 |

*$\log_{10}$ mean ± SE IgG isotype specific antibody titer
ND = not done

TABLE 3

Immune responses at day 60 following p½MOMP or EB immunization.

| Immunogen | EB $IgG_{2a}$ antibody titer ($\log_{10}$) | DTH response to EB (mm × $10^2$) |
|---|---|---|
| EB (n = 13) | 5.6 ± 0.4 | 9.6 ± 2.0 |
| p½MOMP (n = 13) | 2.0 ± 0 | 6 ± 1.6 |
| pcDNA3 (n = 13) | 1.3 ± 0 | 1 ± 1 |

REFERENCES

1. M. A. Liu, M. R. Hilleman, R. Kurth, Ann. N.Y. Acad. Sci. 772 (1995).

2. D. M. Pardoll and A. M. Beckerieg, Immunity 3, 165 (1995); W. M. McDonnell and F. K. Askari, N. Engl. J. Med. 334, 42 (1996).
3. J. B. Ulmer et al., Science 259, 1745 (1993); B. Wang et al., Proc. Natl. Acad. Sci. USA 90, 4156 (1993); G. J. M. Cox, T. J. Zamb, L. A. Babiuk, J. Virol. 67, 5664 (1993); E. Raz et al., Proc. Natl. Acad. Sci. USA, 91,9519 (1994); Z. Q. Xiang et al., Virology 199, 132 (1994); J. J. Donnelly et al., J. Infect. Dis. 713, 314 (1996); D. L. Montgomery et al., DNA. Cell. Biol. 12, 777 (1993); J. J. Donnelly et al., Nature Medicine 1, 583 (1995); G. H. Rhodes et al., Dev. Biol. Stand. 82, 229 (1994); H. L. Davis, M. L. Michel, R. G. Whalen, Human Molecular Genetics 2, 1847 (1993); J. B. Ulmer et al., Vaccine 12, 1541 (1994); Z. Xiang and H. C. J. Ertl. Immunity 2, 129 (1995); E. F. Fynan et al, Proc. Natl. Acad. Sci. USA 90, 11478 (1993); E. Manickan, R. J. D. Rouse, Z. Yu, J. Immunol. 155, 259 (1995).
4. M. Sedegah, R. Hedstrom, P. Hobart, S. L. Hoffman, Proc. Natl. Acad. Sci. USA 91, 9866 (1994); M. A. Barry, W. C. Lai, S. A. Johnston, Nature 377, 632 (1995); D. Xu and F. Y. Liew, Vaccine 12, 1534 (1994); D. B. Lowrie, R. E. Tascon, M. J. Colston, Vaccine 12, 1537 (1994).
5. J. W. Moulder, Microbiol. Rev. 55, 143 (1991).
6. J. Schachter, Curr. Top. Microbiol. Immunol. 138, 109 (1988); S. D. Hillis and J. N. Wasserheit, N. Engl. J. Med. 334, 1399 (1996).
7. R. C. Brunham and R. W. Peeling, Infectious Agents and Disease 3, 218 (1994); R. P. Morrison, D. S. Manning, H. D. Caldwell, in Advances in Host Defence Mechanisms, T. C. Quin, Ed. (Raven Press, New York, 1992), pp 57–84.
8. J. T. Grayston and S. -P. Wang, Sex. Trans. Dis. 5, 73 (1978); J. T. Grayston and S. -P. Wang, J. Infect. Dis. 132, 87 (1975).
9. H. R. Taylor, J. Whittum-Hudson, J. Schachter, Invest. Ophthalmol. Vis. Sci. 29, 1847 (1988); B. E. Batteiger, R. G. Rank, P. M. Bavoil, J. Gen. Microbiol. 139, 2965 (1993); M. Campos et al., Invest. Ophthalmol. Vis. Sci. 36, 1477 (1995); H. Su, M. Parnell, H. D. Caldwell, Vaccine 13, 1023 (1995); T. -W. Tan, A. J. Herring, I. E. Anderson, Infect. Immun. 58, 3101 (1990); M. Tuffrey, F. Alexander, W. Conlan, J. Gen. Microbiol. 138, 1707 (1992).
10. Y. -X. Zhang, J. G. Fox, Y. Ho, Mol. Biol. Evol. 10, 1327 (1993).
11. R. P. Morrison, K. Feilzer, D. B. Tumas, Infect. Immun. 63, 4661 (1995); H. Su and H. D. Caldwell, Infect. Immun. 63, 3302 (1995); J. U. Igietseme et al., Reg. Immunol. 5, 317 (1993); J. U. Igietseme and R. G. Rank, Infect. Immun. 59, 1346 (1991); D. M. Williams, J. Schachter, J. J. Coalson, J. Infect. Dis. 149, 630 (1984).
12. G. Tipples and G. McClarty, J. Biol. Chem. 270, 7908 (1995).
13. X. Yang, K. T. HayGlass, R. C. Brunham, J. Immunol., 156, 4338 (1996).
14. H. Su and H. D. Caldwell, Infect. Immun. 63, 946 (1995).
15. A. S. McWilliam, D. Nelson, J. A. Thomas, J. Exp. Med. 179, 1331 (1994); M. R. Neutra, E. Pringault, J. -P. Kraehenbuhl, Annu. Rev. Immunol. 14, 275 (1996); J. M. Austyn, J. Exp. Med. 183, 1287 (1996).
16. R. Brunham et al., J. Clin. Invest. 94, 458 (1994); R. C. Brunham et al., J. Infect. Dis. 173, 950 (1996).
17. Tang et al., Nature 1992, 356: 152–154.
18. Furth et al., Vaccine 1994, 12: 1503–1509.
19. Morrison R P, Manning D S, Caldwell H D. Immunology of *Chlamydia trachomatis* infections: Immunoprotective and immunopathogenetic responses. In: Quin T C. Advances in host defence mechanisms. Sexually transmitted diseases. Vol. 8. New York: Raven Press, 1992: 52–84.
20. Brunham R., Yang C., Maclean I., Kimani J., Maitha G., Plummer F., *Chlamydia trachomatis* from individuals in a sexually transmitted disease core group exhibit frequent sequence variation in the major outer membrane protein (omp1) gene. J. Clin. Invest. 1994; 94:458–63.
21. Xiang Z. Ertl H C J. Manipulation of the immune response to a plasmid-encoded viral antigen by coinoculation with plasmids expressing cytokines. Immunity 1995: 2:129–35.

What we claim is:

1. An immunogenic composition for in vivo administration to a host for the generation in the host of a protective immune response to a major outer membrane protein (MOMP) of a strain of Chiamydia, comprising:
    a non-replicating plasmid vector comprising:
        a nucleotide sequence encoding said MOMP or a fragment of said MOMP that generates a MOMP-specific immune response, and
        a cptomeqalovirus promoter sequence operatively coupled to said nucleotide sequence for expression of said MOMP in the host; and
    a pharmaceutically-acceptable carrier therefor.
2. The composition of claim 1 wherein said nucleotide sequence encodes full-length MOMP.
3. The immunogenic composition of claim 1 wherein said nucleotide sequence encodes an N-terminal fragment of said MOMP of approximately half the size of full-length MOMP.
4. The immunogenic composition of claim 1 wherein said strain of Chlamydia is a strain producing chlamydial infections of the lung.
5. The immunogenic composition of claim 1 wherein said strain of Chlamydia is a strain of *Chlamydia trachomatis*.
6. The immunogenic composition of claim 5 wherein said non-replicating plasmid vector is plasmid pcDNA3 containing said promoter sequence and into which said nucleotide sequence is inserted in operative relation to said promoter sequence.
7. The composition of claim 1 wherein said immune response is predominantly a cellular immune response.
8. The composition of claim 1 wherein said nucleotide sequence encodes said MOMP which stimulates a recall immune response following exposure to wild-type Chlamydia.
9. A vaccine produced by a method which comprises:
    isolating a nucleotide sequence encoding a major outer membrane protein (MOMP) of a strain of Chiamydia or a fragment of said MOMP that generates a MOMP-specific immune response,
    operatively linking said nucleotide sequence to at least one control sequence including a cytomegalovirus promoter to produce a non-replicating plasmid vector, the control sequence directing expression of said MOMP when introduced to a host to produce an immune response to said MOMP, and
    formulating said vector as a vaccine for in vivo administration to a host.

* * * * *

UNITED STATES PATENT AND TRADEMARK OFFICE
CERTIFICATE OF CORRECTION

PATENT NO.    : 6,235,290 B1
DATED         : May 22, 2001
INVENTOR(S)   : Brunham, Robert C.

It is certified that error appears in the above-identified patent and that said Letters Patent is hereby corrected as shown below:

Column 1,
Line 3, the following has been added:
-- Reference to Related Application
This application claims priority under the provisions of 35 USC 119(e) from United States Patent Application No. 60/021,607 filed July 12, 1996. --

Column 14,
Line 29, "cptomeqalovirus" has been changed to -- cytomegalovirus --

Signed and Sealed this

Eighteenth Day of March, 2003

JAMES E. ROGAN
*Director of the United States Patent and Trademark Office*